United States Patent [19]

Mitchell

[11] Patent Number: 4,638,104
[45] Date of Patent: Jan. 20, 1987

[54] PREPARATION OF TERPINEN-4-OLS AND INTERMEDIATES

[75] Inventor: Peter W. D. Mitchell, Freehold, N.J.
[73] Assignee: Union Camp Corporation, Wayne, N.J.
[21] Appl. No.: 782,647
[22] Filed: Oct. 1, 1985
[51] Int. Cl.[4] .............................................. C07C 35/18
[52] U.S. Cl. ................................... 568/827; 568/825; 568/826
[58] Field of Search ........................ 568/827, 826, 828

[56] References Cited

U.S. PATENT DOCUMENTS

| | | | |
|---|---|---|---|
| 4,306,099 | 12/1981 | Fetizon et al. | 568/827 |
| 4,496,776 | 1/1985 | Edwards et al. | 568/827 |
| 4,570,022 | 2/1986 | Mitchell | 568/827 |

OTHER PUBLICATIONS

Mitzner, "J. Organic Chem." vol. 31, (1966), pp. 2022–2023 and 2419–2420.
Paul et al "J. Amer. Chem. Soc." vol. 78, (1959), pp. 116–120.
Wilson et al "J. Amer. Chem. Soc." vol. 101, (1979), pp. 3340–3344.

*Primary Examiner*—Werren B. Lone
*Attorney, Agent, or Firm*—Kane, Dalsimer, Kane, Sullivan and Kurucz

[57] ABSTRACT

A method of preparing terpinen-4-ols and intermediates thereof, by reacting 1,4-cineole with an alkali metal aryl compound, resulting in an E2 elimination reaction of 1,4-cineole.

8 Claims, No Drawings

PREPARATION OF TERPINEN-4-OLS AND INTERMEDIATES

BACKGROUND OF THE INVENTION

1. Field of the Invention

The present invention relates to a method for the preparation of 1-terpinen-4-ol, 1(7)-terpinen-4-ol, and intermediates thereof.

2. Brief Description of the Prior Art

1-Terpinen-4-ol is a fragrance chemical possessing a pleasing earthy-green note with a slightly peppery-woody undernote. It is an important constituent of synthetic essential oils, especially geranium, lavender, and rose oils and has the desirable effect in all fragrance compositions of enhancing naturalness and diffusiveness. Because of the high cost and uncertainty of supply of the natural product, which is isolated from tea tree oil, synthetic routes to 1-terpinen-4-ol have been developed, notably via photo-oxidation or epoxidation of terpinolene. Both of these processes suffer from only modest overall yields and multiple chemical steps. The photochemical route requires expensive specialized equipment.

1(7)-terpinen-4-ol is a minor constituent of rosemary oil and occurs in trace quantity in commercial pine oil, which consists of mainly alpha-, beta-, and gamma-terpineols; see *J. Org. Chem.*, 31, 2419 (1966). It is not available in good purity from either natural or synthetic sources. It is rarely mentioned in the chemical literature, and its unambiguous synthesis has been described only once [*Indian J. Chem.*, 9(9), 899, 1971]. This laboratory synthesis involved four steps and required expensive mercury- and phosphorous-containing reagents. The overall molar yield was only 22%.

The procedure of the present invention has three major advantages over the prior art preparations. First, it is a single step process. Second, it proceeds in very high selectivity to either or both of the desired 4-ol products, depending on the reaction conditions. Third, it uses as starting material a low-cost by-product, namely, 1,4-cineole, which is generated during the production of pine oil by hydration of the abundant turpentine component, alpha-pinene.

SUMMARY OF THE INVENTION

The object of the present invention is to provide a method for the preparation of terpinen-4-ols and intermediates thereof.

The present invention comprises a method of preparing terpinen-4-ols, which comprises an E2 elimination of 1,4-cineole.

DETAILED DESCRIPTION OF THE PREFERRED EMBODIMENTS OF THE PRESENT INVENTION

The method of the present invention is carried out by the opening of the ether bridge on the 1,4-cineole molecule. The reaction, an E2 elimination, may be effected by reacting the 1,4-cineole with an elimination reagent. Representative of elimination reagents are alkali metal aryl compounds. The term "aryl" as used herein means the moiety obtained by removing a hydrogen atom from a parent monocyclic or polycyclic aromatic hydrocarbon, or from a substituted aromatic hydrocarbon. Representative of aryl are phenyl, tolyl, xylyl, p-phenoxyphenyl, biphenyl, p-terphenyl, naphthyl, anthryl, phenanthryl, and pyrenyl. The term "alkali metal" as used herein means lithium, sodium, potassium, rubidium and cesium.

Preferred elimination agents are then represented by alkali metal aryls such as phenyl lithium, tolyl sodium, naphthyl sodium and equivalent alkali metal aryls.

Alkali metal aryl compounds may be prepared by many known methods, for example, reaction of an aryl halide with an alkali metal as described in Pines and Stalick, "Base-Catalyzed Reactions of Hydrocarbons and Related Compounds," Academic Press, 1977. Another method is direct reaction of certain polycyclic aromatic hydrocarbons with the metal. Details of the reaction of sodium metal with naphthalene, anthracene, and phenanthrene, for example, were reported by Paul, Lipkin, and Weissman; see *J. Amer. Chem. Soc.*, 78, 116 (1956).

The most preferred elimination agent is the material obtained by reacting sodium metal and anthracene. The structure of this material is not exactly characterized but is generally recognized as having the following formulae:

or

The method of the present invention may be carried out by an admixture of the 1,4-cineole with the requisite elimination reagent. The reaction may be represented schematically by the following formulae in which sodium-anthracene is shown as illustrative of the action of the metal aryl elimination reagant:

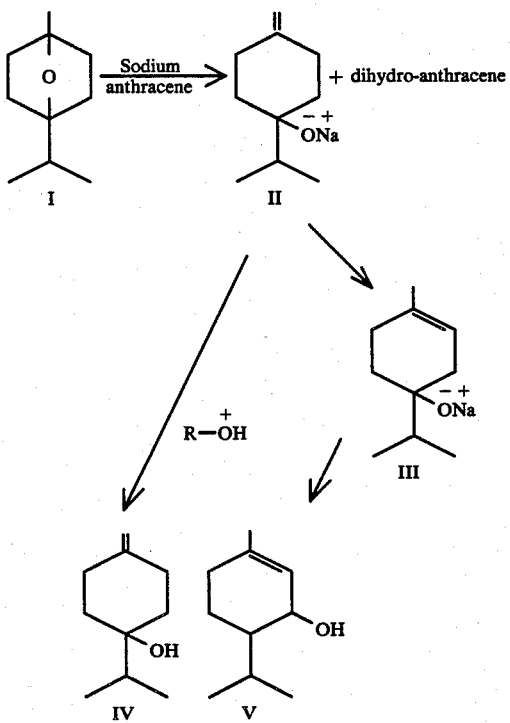

The first-formed intermediate isomer (II), which contains the double bond in the exocyclic position, converts to isomer (III) if the reaction is allowed to proceed. Addition of water (R=H); an acid, for example, acetic acid (R=CH₃CO); or an alcohol, for example, isopropanol (R=isopropyl), to the reaction mixture, converts the intermediate sodium terpinenates to the free alcohols, 1(7)-terpinen-4-ol (IV) and 1-terpinen-4-ol (V), respectively.

The sodium-anthracene reagent is particularly advantageous in that during the course of the reaction the dihydroanthracene which is formed converts to anthracene with the loss of a molecule of hydrogen. This anthracene reacts with further amounts of sodium. The anthracene, then, acts in this reaction as a true catalyst. At the end of the reaction the anthracene is recovered along with dihydro-anthracene and the mixture can be re-used.

Sodium metal itself is not an effective elimination reagent, as shown in the example.

Although the desired elimination reaction may be carried out by simple admixture of the reactants, a solvent for the 1,4-cineole and the anthracene may be added to the reaction mixture. Advantageously the solvent is an inert hydrocarbon for example, toluene, xylene, heptane, mineral spirits, and equivalent solvents. Alternatively, the solvent may be the terpenic materials associated with 1,4-cineole during its production, especially p-cymene, limonene, alpha-terpinene, and other terpene hydrocarbons. The solvent may also be an ethereal material, for example, tetrahydrofuran, diethyl ether, and the like. These solvents are normally present in many preparations of alkali metal aryls and thus may serve as solvent for both the preparation of the elimination reagent and its reaction with 1,4-cineole.

Although we have found that the temperature and/or pressure of the reaction is not critical, the above-described reaction proceeds advantageously at a temperature within the range of from about 30° to about 250° C.; preferably from about 60° to about 180° C. Lower reaction temperatures favor formation of the 1(7)-isomer, whereas higher reaction temperatures favor formation of the 1-isomer.

The proportions of the reactants employed in the method of the present invention are also not critical, stoichiometric proportions of the alkali metal being acceptable if the 1(7)-isomer is desired. To obtain a mixed terpinen-4-ol product, a small excess of the elimination reagent is employed. A larger excess can be used if formation of only the 1-isomer is desired. In a preferred embodiment of the present invention, the anthracene catalyst is employed in the proportion of from about 1 to about 100 percent by weight of the 1,4-cineole. The most preferred amount of anthracene is from about 5 to about 60 percent by weight of the 1,4-cineole.

The reaction is conveniently carried out in conventional reaction apparatus. Progress of the reaction may be followed employing known analytical techniques. In general the reaction is complete within 1 to 36 hours. Upon termination of the reaction by addition of an acid, alcohol, or water, the desired terpinen-4-ols may be separated from the reaction mixture and from each other by conventional techniques such as by liquid chromatography or distillation. Any unconverted 1,4-cineole is readily recovered and can be used again in the process.

The following examples describe the manner and process of making and using the present invention, and set forth and describe the best mode of carrying out the invention, but are not to be construed as limiting, with equivalents to one skilled in the art being contemplated within the present invention.

EXAMPLES

Example 1

Sodium metal (0.8 g) was added to a stirred mixture of 1,4-cineole (3.4 g, 90 percent purity) and limonene (10 g). This mixture was then heated to reflux, about 177° C., for 16 hours. The mixture was then cooled and washed with water to give a product oil containing in relative amounts, only about 3.2 percent of the two terpinen-4-ols, and 96.4 percent unchanged 1,4-cineole for a total 4-ol yield of about 4 molar percent.

Example 2

Sodium metal (0.6 g) was added to a stirred mixture of 1,4-cineole (3.4 g, 90 percent purity), limonene (10 g), and anthracene (0.6 g). This mixture was heated to reflux for 5½ hours then cooled and quenched with water to give a product oil containing 22.7 percent 1-terpinen-4-ol, 3.7 percent anthracene, 0.5 percent dihydro-anthracene, and only a trace of unconverted 1,4-cineole. The molar yield of 1-terpinen-4-ol was about 95 mole percent based on the 1,4-cineole charged.

Example 3

Sodium metal (6.2 g) was added to a stirred mixture of 1,4-cineole (34 g), limonene (100 g), and anthracene (3 g). This mixture was heated to reflux for 35 hours at which time an additional 2 g of sodium was added. After 5.5 additional hours of reaction, the mixture was cooled to ambient temperature and treated with 125 mls. of water. The product oil was separated and washed once with water. The recovered oil weighed 132.34 g and an estimated 4 g. had been used for gas chromatography analyses, giving a total of 136.34 g. It analyzed 20.76 wt.-percent 1-terpinen-4-ol and the starting material analyzed 90.16 wt percent 1,4 cineole. Thus the 1-terpinen-4-ol yield was 92.6 mole percent.

Example 4

The procedure of Example 2 was followed but a mixture of anthracene and dihydro-anthracene (0.4 g) recovered from the reaction of example 3 was used instead of fresh anthracene with 0.8 g sodium, 3.4 g 1,4-cineole, and 10 g limonene. The reaction was quenched with water after 5.5 hours and the oil found to contain, in relative amounts, 42.2 percent unconverted 1,4-cineole and 57.8 percent product terpinen-4-ols. This demonstrates that the recovered catalyst is still active for 1,4-cineole conversion.

Example 5

The procedure of Example 2 was followed, but only 0.3 g of anthracene was charged. The reaction, after 7½ hours, gave a product oil containing, in relative amounts, 23.3 percent unreacted 1,4-cineole, 41.3 percent 1(7)-terpinen-4-ol, and 35.4 percent 1-terpinen-4-ol. The molar yields of isomeric 4-ols of isomeric 4-ols are thus about 38 percent and 33 percent, respectively, with at least 90 percent selectivity to the two 4-ols.

Example 6

The procedure of Example 2 was followed, but toluene was used in place of limonene, and 1.96 g of anthracene was used. After 2½ hours at reflux (about 110° C.), the reaction mixture was quenched with water and the product oil, which by gas chromatographic analysis indicated a conversion of about 80 percent, was eluted with heptane through an alumina-packed chromatography column. Fractions containing alcohols were collected and combined to give a product oil containing 68.7 percent 1(7)-terpinen-4-ol and 30.7 percent 1-terpinen-4-ol.

Example 7

Sodium (0.8 g) was added to a mixture of 1,4-cineole (3.4 g, 90 percent purity), limonene (10 g), and anthracene (2 g) and the mixture immersed in an ultrasonic bath. The mixture was sonicated for 7.5 hours, then removed from the bath, stirred and heated to 60° C. for 3 hours, then at 110° C. for a further 3 hours. The reaction mixture was cooled and washed with water to give a product oil containing 10.2 percent 1(7)-terpinen-4-ol, 2.5 percent 1-terpinen-4-ol and 4.2 percent unreacted 1,4-cineole. The molar yield of the terpinen-4-ol isomers was about 60 percent and 15 percent respectively.

Example 8

One gram of each of the aromatic compounds listed in Table I (below) were reacted with sodium (1 g), 1,4-cineole (3.4 g) and limonene (10 g), at the reflux temperature of the mixture. The relative amounts of products and starting material in the reaction mixture after a given time are listed.

TABLE I

| Aromatic Compound | Time (mins.) | 1-Terpinen-4-ol | 1-(7)-Terpinen-4-ol | 1,4-Cineole |
| --- | --- | --- | --- | --- |
| Pyrene | 160 | 100 | 0 | 0 |
| Acenaphthylene | 165 | 1.7 | 7.4 | 90.9 |
| Chrysene | 165 | 2.3 | 1.8 | 95.8 |
| Phenanthrene | 240 | 2.5 | 2.5 | 95.0 |
| o-chlorotoluene | 290 | 46.2 | 13.5 | 40.2 |

What is claimed is:

1. A method for the preparation of 1-terpinen-4-ol and 1(7)-terpinen-4-ol, comprising an E2 elimination of 1,4-cineole, wherein the elimination reagent is an alkali metal aryl compound wherein aryl is selected from the group consisting of phenyl, tolyl, xylyl, p-phenoxyphenyl, biphenyl, p-terphenyl, naphthyl, anthryl, phenanthryl and pyrenyl.

2. The method as described in claim 1, wherein the alkali metal aryl is prepared by reacting an alkali metal with a polycyclic aromatic hydrocarbon.

3. The method as described in claim 2, wherein the alkali metal is selected from the group consisting of sodium, lithium, and potassium.

4. The method as described in claim 2, wherein the polycyclic aromatic hydrocarbon is anthracene.

5. The method as described in claim 4, wherein the alkali metal is sodium.

6. The method as described in claim 5, wherein the reaction temperature is within the range of from about 60° to about 180° C., and the proportion of anthracene is between about 5 and about 60 percent by weight of the 1,4-cineole.

7. The method as described in claim 2, wherein the polycyclic aromatic hydrocarbon is pyrene.

8. The method as described in claim 7, wherein the alkali metal is sodium.

* * * * *